US010350092B1

(12) United States Patent
Caputo et al.

(10) Patent No.: US 10,350,092 B1
(45) Date of Patent: Jul. 16, 2019

(54) METHODS, APPARATUSES AND SYSTEMS FOR AMPUTEE GAIT CAPACITY ASSESSMENT

(71) Applicant: Carnegie Mellon University, Pittsburgh, PA (US)

(72) Inventors: Joshua M. Caputo, Pittsburgh, PA (US); Steven H. Collins, Pittsburgh, PA (US); Peter G. Adamcyzk, Ann Arbor, MI (US); Myunghee Kim, Pittsburgh, PA (US); Tianjian Chen, Pittsburgh, PA (US); Tianyao Chen, Washington, DC (US); Vincent Chiu, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 41 days.

(21) Appl. No.: 15/333,463

(22) Filed: Oct. 25, 2016

Related U.S. Application Data

(63) Continuation-in-part of application No. 14/827,299, filed on Aug. 15, 2015.

(60) Provisional application No. 62/230,046, filed on May 26, 2015, provisional application No. 62/070,134, filed on Aug. 15, 2014.

(51) Int. Cl.
*A61F 2/72* (2006.01)
*A61F 2/66* (2006.01)
*A61F 2/70* (2006.01)

(52) U.S. Cl.
CPC .................. *A61F 2/72* (2013.01); *A61F 2/66* (2013.01); *A61F 2002/6614* (2013.01); *A61F 2002/701* (2013.01)

(58) Field of Classification Search
CPC ............. A61F 2/66; A61F 2/68; A61F 2/6607
USPC ........ 600/301; 623/47, 53, 54; 254/10.5, 11, 254/33, 98
See application file for complete search history.

(56) References Cited

U.S. PATENT DOCUMENTS

| 9,713,439 | B1* | 7/2017 | Wu | A61B 5/112 |
| 2013/0158444 | A1* | 6/2013 | Herr | A61H 1/0255 |
| | | | | 601/23 |
| 2013/0274894 | A1* | 10/2013 | Goldfarb | A61F 2/60 |
| | | | | 623/24 |

(Continued)

OTHER PUBLICATIONS

A Man-Interactive Simulator System for Above-Knee Prosthetics Studies, Flowers, Woodie C., MIT, 1972.

(Continued)

*Primary Examiner* — Gary Jackson
*Assistant Examiner* — Zahed Kabir
(74) *Attorney, Agent, or Firm* — Fish & Richardson P.C.

(57) ABSTRACT

The present invention includes a tethered ankle-foot prosthesis emulator having two independently-actuated forefoot digits that are coordinated to provide plantarflexion and inversion-eversion torques, and an independently-actuated heel. An end-effector was designed which is worn by a subject, and which was integrated with off-board motor and control hardware, to facilitate high bandwidth torque control. The platform is suitable for haptic rendering of virtual devices in experiments with humans, which may reveal strategies for improving balance or allow controlled comparisons of conventional prosthesis features. A similar morphology is also effective for autonomous devices.

26 Claims, 15 Drawing Sheets

(56) References Cited

U.S. PATENT DOCUMENTS

| | | | |
|---|---|---|---|
| 2014/0088729 A1* | 3/2014 | Herr | A61F 2/60 623/50 |
| 2015/0265425 A1* | 9/2015 | Aagaah | A61F 2/6607 623/47 |
| 2017/0027803 A1* | 2/2017 | Agrawal | A61B 5/6828 |

OTHER PUBLICATIONS

An Emulator System for Developing Improved Elbow-Prosthesis Designs, Abul-Haj, et al., IEEE Trans. Biom. Eng., Sep. 1987.

An Actuator system for Investigating Electrophysical and Biomedical Features Around the Human Ankle Joint During Gait, Anderson, et al., IEEE Trans. Rehab. Eng., Dec. 1995.

Powered Lower Limb Orthoses: Applications in Motor Adaption and Rehabilitation, Sawicki, et al., IEEE 9th Int'l Conf. Rehab. Robotics, Jun. 2005.

Design and Evaluation of the Gait Rehabilitation Robot LOPES, Veneman, ISBN 978-90-365-2594-7, 2007.

Fundamentals of Ergonomic Exoskeleton Robots, Schiele, ISBN 978-90-8559-379-9, 2008.

A Highly Backdrivable, Lightweight Knee Actuator for Investigating Gait in Stroke, Sulzer, et al., IEEE Trans. Robotics, Jun. 2009.

Developing Ankle Control Strategies for Assistive and Rehabilitative Devices, Collins, et al., Int'l Conf. Dynamic Walking, 2011.

Externally Powered and Controlled Ankle-Foot Prosthesis, Caputo, et al., Int'l. Cont. Dynamic Walking, 2011.

Externally Powered and Controlled Ankle-Foot Prosthesis (Poster), Caputo, et al., Int'l. Conf. Dynamic Walking, 2011.

Targeting Specific Muscles for Rehabilitation With an EMG-Controlled Ankle-Foot Orthosis, Jackson, et al., Int'l. Conf. Dynamic Walking, 2012.

Targeting Specific Muscles for Rehabilitation Using an Ankle-Foot Orthosis (slides), Jackson, et al., Int'l. Conf. Dynamic Walking, 2012.

An Externally-Powered and Controlled Ankle-Foot Prosthesis for Use in Push-Off Experiments, Caputo, et al., Am. Soc. Biomechanics, 2012.

Ankle-Foot Prosthesis Testbed (poster), Caputo, et al., Am. Soc. Biomechanics, 2012.

\* cited by examiner

A  Emulator system

B  End-effector schematic

C  Degrees of freedom

D  Prothesis end-effector prototype

METHODS, APPARATUSES AND SYSTEMS FOR AMPUTEE GAIT CAPACITY ASSESSMENT

RELATED APPLICATIONS

This application is a continuation-in-part of pending U.S. patent application Ser. No. 14/827,299, filed Aug. 15, 2015, which claims the benefit of U.S. Provisional Application Ser. No. 62/070,134, filed Aug. 15, 2014 and U.S. Provisional Application Ser. No. 62/230,046, filed May 26, 2015.

STATEMENT REGARDING GOVERNMENT-SPONSORED RESEARCH AND DEVELOPMENT

This invention was made with partial government support under NIH grant 1R43HD076518-0, NSF grant CMMI-1300804 and NSF grant CBET1511177. The government has certain rights in this invention.

FIELD OF THE INVENTION

This invention relates to methods, apparatuses and systems for assessing gait capacity of lower-limb amputees, as an aid in prescribing appropriate prosthetic devices. In particular, the invention relates to robotic emulation of commercially-available prostheses.

BACKGROUND OF THE INVENTION

Over one million people in the U.S. live with limb loss, with an estimated 100,000 new cases each year, over 80% involving the lower limb. Commercial prostheses are available with many different designs and features, at prices ranging from a few hundred dollars to over one hundred thousand dollars. Yet the prescription process is based mostly on subjective assessments and past performance, with no way to prospectively determine whether an increment in cost will yield a satisfactory improvement in quality of life for a given individual.

The most important mobility issues are discomfort, stability and fatigue. Persons with below-knee amputation choose a lower self-selected walking speed than able-bodied persons, and expend at least 20% more energy to walk at the same speed. Many advanced conventional prostheses have features such as higher elastic energy storage and return, and users generally prefer these feet for reasons of comfort. Nonetheless, the speed and energy cost discrepancies from non-amputees persist despite a wide range of complexity and cost in commercial prosthetic feet.

Recently, advanced foot prostheses have come to market promising to break this barrier by restoring one crucial component all passive prostheses lack: an ankle joint that can perform net positive work on the body. One such device (the BiOM T2 System) can improve walking mechanics, returning walking speed and energy expenditure to near-normal levels for some patients. It is unclear, however, whether all individuals will benefit, and possible benefits come at a steep cost: such devices are currently considerably more expensive, accessible to only the best-reimbursed or wealthiest patients. This would be a bad investment for any patient who does not realize major gains in quality of life, especially since advanced devices often cannot be returned or resold following initial use. Emerging robotic prostheses like the BiOM intensify a longstanding dilemma in prosthetics practice: how can practitioners and insurance companies identify who will benefit sufficiently from increased performance to justify the higher cost of advanced devices? This problem has recently become more acute, as Medicare and other payers have identified cases of fraud, and in response have increased the demand for documentation to support classification of each individual's gait capacity. The argument is that current practice for assigning a K-level (K0 to K4) relies too heavily on unreliable information such as prosthetist's opinion and the patient's stated activities and goals, and so can be manipulated, to the detriment of the payer.

Recent advances have added some nuance to the differentiation among K-levels, such as short in-clinic functional mobility tests or approximate activity classification based on time-binned step clustering. These tests include tasks such as freely-selected walking, standing and sitting transitions, climbing and descending stairs, navigating obstacles, and single-limb standing. However, all of these categorization methods have a common limitation: they are based on current mobility with the patient's current conventional prosthesis. They do not incorporate any information on how an individual patient will use and respond to a more advanced prosthesis, such as the BiOM T2. There is essentially no information available to help clinicians and payers determine whether a particular patient will benefit from an advanced prosthesis. There is therefore a high probability of suboptimal patient outcomes, economic inefficiency, and provider-carrier conflict during the prescription of advanced prostheses.

Robotic prostheses can improve locomotor performance for individuals who have restricted mobility due to lower-limb amputation. During walking, these devices can restore normal ankle and knee kinematics, reduce metabolic rate, and provide direct neural control of the limb. As robotic technologies improve, active prostheses are expected to enhance performance even further.

Ankle inversion-eversion, or roll, is an important aspect of prosthesis function. Commercial prostheses typically include a passive inversion-eversion degree of freedom, either using an explicit joint or a flexure. This mitigates undesirable torques created by uneven ground. Inversion torque has a strong effect on side-to-side motions of the body during human walking, and its pattern is altered among individuals with amputation. Side-to-side motions seem to be less stable in bipedal locomotion, particularly for amputees. Difficulty controlling inversion-eversion torque in the prosthetic ankle may partially explain reduced stability and increased fear of falling and fall rates among people with amputation.

Robotic prosthesis designs have begun to incorporate active control of ankle inversion-eversion. A tethered ankle prosthesis with inversion provided by a four-bar linkage and controlled by a linear actuator has been described, in which a plantarflexion degree of freedom is provided using a passive spring. A prototype device intended to provide both plantarflexion and inversion-eversion control using two motors and a gimbal joint has also been described.

The mass of prostheses with active inversion-eversion control is generally related to joint design. Linkages and gimbal joints often involve large parts with complex loading, resulting in increased strength and mass requirements. An alternative is suggested by the split-toe flexures in conventional passive prostheses and the actuation schemes in some powered ankle orthoses. During walking, peak inversion-eversion torques are of much lower magnitude than peak plantarflexion torques, and the majority of the inversion impulse occurs during periods of high plantarflexion torque. Coupling plantarflexion and inversion-eversion torque through the actions of two hinged forefoot digits might provide sufficient torque capacity, enabling a simple, lightweight design.

Mechatronic performance in experimental prosthesis systems can also be improved by separating actuation hardware from worn elements. A tethered emulator approach decouples the problems of discovering desirable prosthesis functionality from the challenges of developing fully autonomous systems. Powerful off-board motors and controllers can be connected to lightweight instrumented end-effectors via flexible tethers, resulting in low worn mass and high-fidelity torque control. Such systems can be used to haptically render virtual prostheses to human users, facilitating the discovery of novel device behaviors that can then be embedded in separate autonomous designs. This approach can also be used for rapid comparison of commercial prostheses in a clinical setting. To be most effective, such prosthesis emulators should have high closed-loop torque bandwidth and lightweight, strong, accurately-instrumented end-effectors.

Torque control in robotic emulator systems can be improved with appropriate series elasticity. Adding a spring in series with a high-stiffness transmission can reduce sensitivity to unexpected actuator displacements imposed by the human. Unfortunately, this compliance also reduces force bandwidth when the output is fixed, because the motor must displace further when stretching the spring. In a tethered system, the flexible transmission itself is likely to have significant compliance, which might provide appropriate series elasticity.

Prosthesis emulators have not yet explored the full range of control strategies. For example, humans appear to control center of pressure during walking or maintain similar rollover shapes despite varying walking conditions. To study these control strategies, an emulator must be equipped with at least two degrees of freedom in both frontal and sagittal planes.

SUMMARY OF THE INVENTION

The present invention describes methods, apparatuses and systems for assessing gait capacity of lower-limb amputees, as an aid in prescribing appropriate prosthetic devices. The invention describes a system to emulate the characteristics of various types of prosthetic devices to provide an amputee the opportunity to simulate the use of such various prosthetic devices. The system collects and analyzes a variety of data during the simulated use of prosthetic devices to provide quantitative information on the appropriateness of various prosthetic devices for the individual amputee.

The platform is suitable for haptic rendering of virtual devices in experiments with humans, which may reveal strategies for improving balance or allow controlled comparisons of conventional prosthesis features. A similar morphology may be effective for autonomous devices.

In one embodiment, the present invention includes a tethered ankle-foot prosthesis with two independently-actuated forefoot digits that are coordinated to provide both plantarflexion and inversion-eversion torques. This configuration allows a simple lightweight structure. The two digits extend the capabilities of the original invention to emulation of so-called multi-axial or split-toe prosthetic feet.

In a second embodiment, the present invention also includes an actuated heel. Actuation of the three digits allows the adjustment of the origin and magnitude of the ground reaction force vector. This additional degree of control extends the capability of the original invention to more accurate emulations, for example, emulation of prosthetic foot rollover shape. The platform is suitable for haptic rendering of virtual devices in experiments with humans, which may reveal strategies for improving balance or allow controlled comparisons of conventional prosthesis features. A similar morphology may be effective for autonomous devices.

BRIEF DESCRIPTION OF THE DRAWINGS

FIG. 4 shows impedance-matching performance of ankle movement vs. angle in three emulator modes and one custom mode;

DETAILED DESCRIPTION OF THE INVENTION

For purposes of this invention, the term digit shall refer generically to a forefoot digit, a heel, or any other portion of the end-effector controlled by a motor controlled by one or more control components.

This invention describes methods, apparatuses and systems for assessing gait capacity of lower-limb amputees, as an aid in prescribing appropriate prosthetic devices. The invention describes a system to emulate the characteristics of various types of prosthetic devices to provide an amputee the opportunity to test-drive various prosthetic devices. The system collects and analyzes a variety of data during the simulated use of prosthetic devices to provide quantitative information on the appropriateness of various prosthetic devices for the individual amputee.

Figure 1:
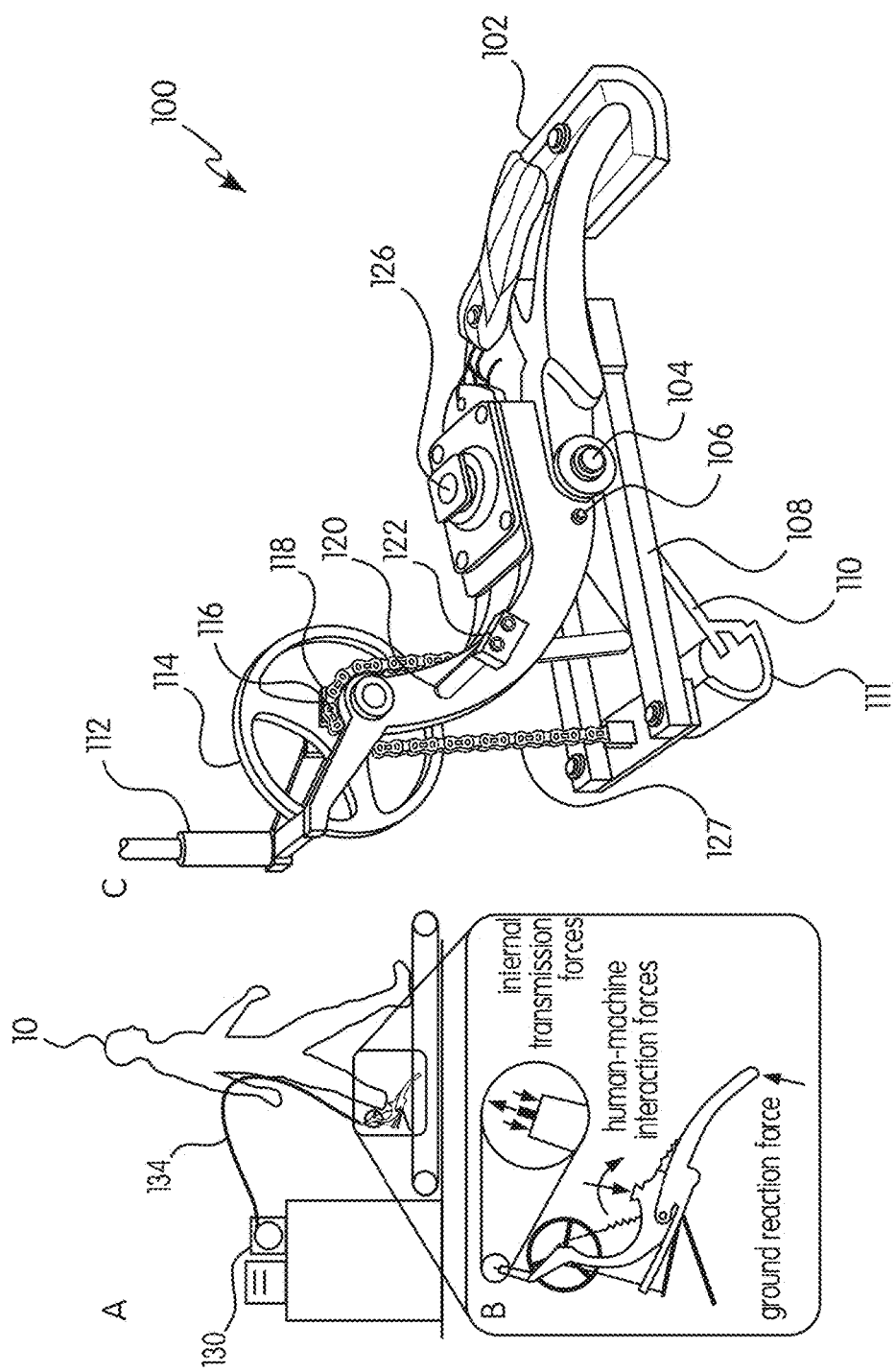
FIG. 1 shows the apparatuses of a first embodiment of the present invention in schematic form.

The apparatus is an off-board, actuated, powered ankle-foot prosthesis emulator that attaches to the tibial pylon of an amputee's prosthetic lower limb in place of their pre-scribed prosthetic foot (FIG. 1). The emulator provides programmable, realtime-controlled torque about the ankle, suitable for emulating different classes of commercial prosthesis ranging from dissipative block-and-foam prostheses (e.g. Solid Ankle Cushion Heal, or "SACH"), to resilient dynamic elastic response designs (e.g. Dynamic Elastic Response or "DER", Elastic Storage and Return, or "ESR" or "ESAR"; for example, Flexfoot), to dynamic elastic feet with multi-axial capabilities, to prostheses that automatically adjust ankle angle (e.g. OssurProprio, Endolite élan, OrthoCare, Innovations Magellan), to active, powered devices (e.g. BiOM T2 System, SPARKy and Freedom Innovations Foot). The emulator allows an amputee to experience the advantages and disadvantages of each level of technology in rapid succession. This system provides objective data about the capacity of an individual patient for gait improvement, and thereby helps practitioners determine the prescription that best balances mobility gains and financial costs.

Figure 5:
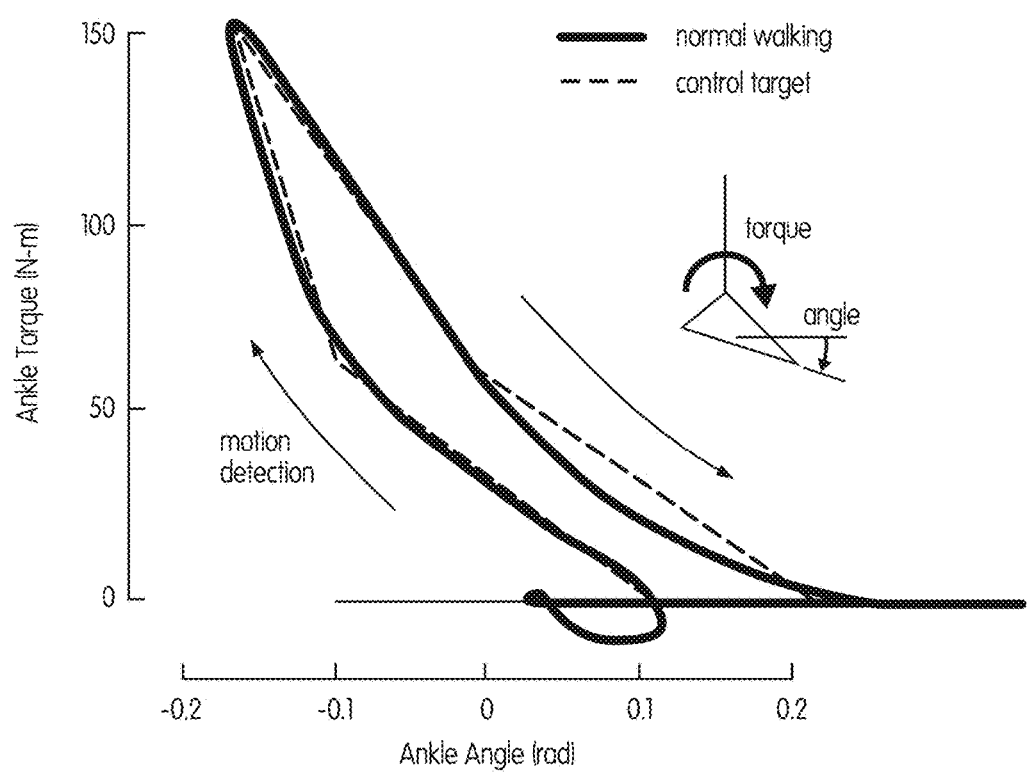
FIG. 5 shows impedance matching design for emulation of a normal ankle.

The emulation programs are based on published curves of ankle torque vs. ankle angle over a complete gait cycle. The differences between device classes include the ankle's angular quasi-stiffness and the net work performed during a gait cycle. Net prosthesis work is an important differentiating factor among these classes; SACH feet provide about 55% energy return, DER about 80%, and powered robotic about 120% energy return, i.e. it supplies positive net work. Example emulation performance (see FIG. 5), demonstrates excellent emulation of SACH and DER modes and reproduction of characteristic positive work output for the BiOM.

The emulation system enables the characterization of responses to conditions that both exceed and under-perform currently available commercial prostheses. In cases where functional benefits may be unclear from comparisons of settings emulating conventional, DER and powered prostheses, it may be valuable to test the individual's response to excessive energy gain or loss in the prosthesis. Patients who readily adapt to unusual conditions may be better candidates for prostheses with complex control behaviors. Clinical feedback to manufacturers could also spur development of products that are better suited to their clients. Because these cases cannot be achieved by commercial devices, such tests can only be done with an emulator such as described herein.

This invention enables evidence-based medicine in prosthetics. The availability of objective gait capacity data closes the feedback loop between the prosthetics clinic and the physician. This invention enables a work flow that starts in the prosthetics clinic with the emulator system. Test results for metrics such as effort, gait stability, maximum speed, and user preference with different classes of prosthesis will become part of the patient's medical record, accessible to the physician, the prosthetist and the payer. The physician will consider this information about gait capacity alongside other medical indications, and make a better-informed, more appropriate, and more defensible prosthesis prescription. The prosthetist will use test results to choose specific componentry and tune the prosthesis to meet the patient's documented needs. For example, a subject who achieves high speeds with moderate effort, but demonstrates lateral instability, may be given a DER foot with an especially wide base of support. This invention provides quantitative evidence to these decisions, which would otherwise be made by subjective visual assessment.

A first embodiment of the present invention is shown in FIG. 1. Shown in FIG. 1C, is end-effector 100 which is worn by subject 10. End-effector 100 connects to the subject using standard universal adapter 124. A custom-sized spacer 128, shown in FIG. 2, connects to universal adapter 124 and allows connection to prosthesis 12 worn by subject 10.

Forefoot portion 102 of end-effector 100 pivots around ankle joint 104. The tension on forefoot 102 is controlled by a series of leaf springs 108 which are connected via chain 127 to sprocket 116. The tension exerted through leaf springs 108 is controlled by transmission element 134, as shown in FIG. 1, which is attached via transmission to attachment 112 to pulley 114. Dorsiflexion spring 126 ensures that forefoot 102 returns to its un-flexed position after tension has been released by chain 127. The angle of the ankle displacement is sent by ankle encoder 106 and is sent back to prosthesis control components 132 and 136 via tether 134b.

Heel 111 of end-effector 100 is connected to the ankle joint 104 via passive heel spring 110. Pulley encoder 118 encodes the rotation of pulley 114 and sends that information to prosthesis control components 132 and 136 via tether 134b.

Figure 2:
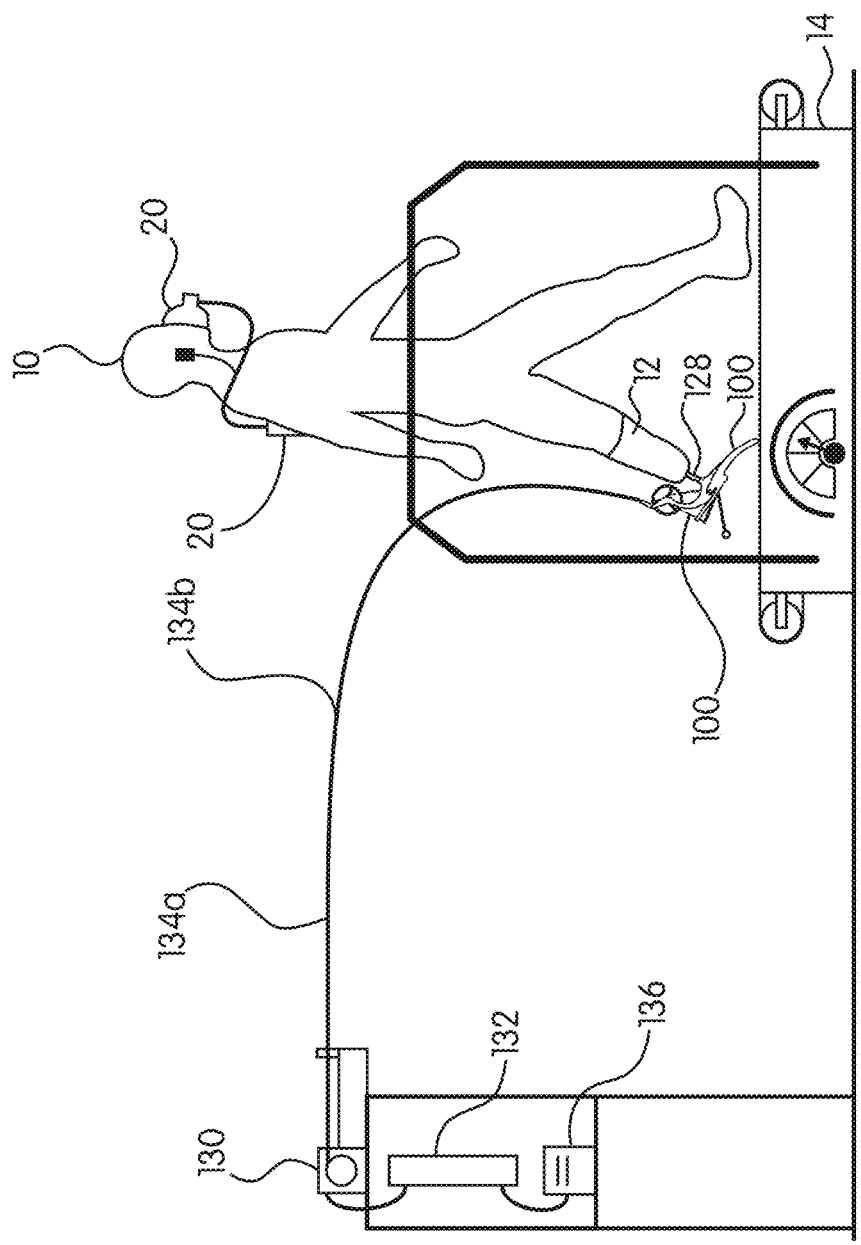
FIG. 2 shows use of the device of the present invention by a subject.

Off-board motor 130 as shown in FIG. 2 controls end-effector 100 under closed-loop computer control. Flexible tether 134b provides feedback from sensors mounted on end-effector 100 and transmission cable 134a controls the tension exerted by pulley 114. Using off-board motor 130 and control components 132 and 136 allows a more flexible, much higher-performance system with a simpler design and less body-mounted mass than an untethered system. With this design, the mechatronic performance of the prosthesis is dominated not by the mechanical properties of end-effector 100, but instead by the closed-loop actuation specified under computer control. Thus, a single ankle-foot end-effector 100 can emulate many control behaviors and mechanical elements. In a preferred embodiment, prosthesis control components 132 and 136 contain models of a plurality of commercially-available prosthesis and is able to simulate the feel of these prostheses to subject 10.

Figure 3:
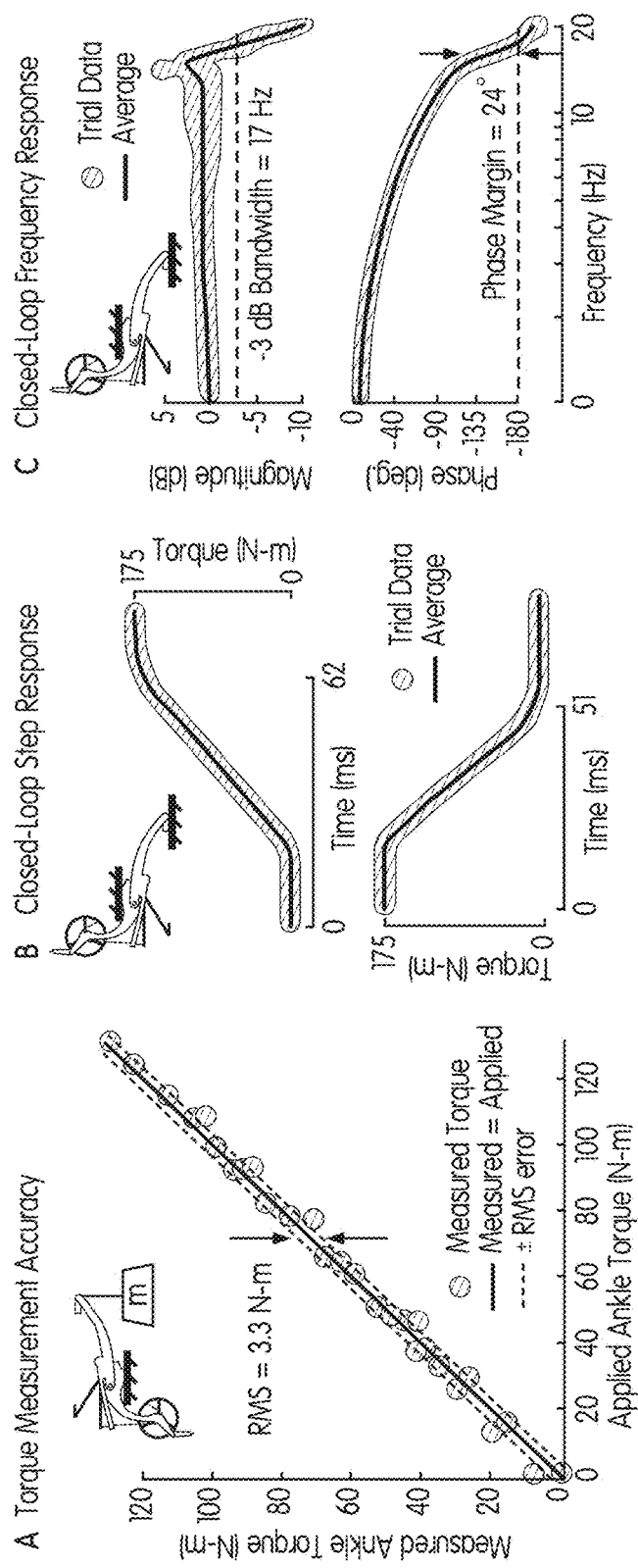
FIG. 3 shows results of benchtop testing of an exemplar embodiment of the present invention.

In an exemplar embodiment, the emulator system comprises a 1.6 kW servomotor and motor controller (Baldor Electric Co.), a 1 GHz control hardware package (dSPACE, Inc.) to perform real-time torque command tracking, and a 3 m long Bowden cable (steel and polyethylene sheath and 6 mm Vectran drive cable, similar to a bicycle brake cable) to transfer power to end-effector 100. The prosthesis end-effector uses a fiberglass leaf spring 108 for series elasticity while transforming cable tension into a torque on the forefoot segment 102, equivalent to ankle plantarflexion in the human foot, as shown in FIG. 1B. Ankle joint angles are measured directly with sensors or encoders 106, while joint torque is inferred from spring deflection based on calibration results. As shown in FIG. 3, the heel 111 comprises a passive leaf spring 108, which provides cushioning at load acceptance. Benchtop testing of the exemplar system (See FIG. 4) established a 17 Hz bandwidth for torque response, 95% rise and fall time of less than 0.070 s, peak power output of 1060 W and peak ankle torque of 175 N·m, with worn mass less than 1 kg. This combination of low worn mass and high closed-loop torque bandwidth are the keys to high-fidelity emulation of specialized prosthetic devices. See Table 1.

| Joint Torque Control System | Torque [N·m] | Bandwidth [Hz] | Worn Mass [kg] | Power [peak, W] | Tethered | Joint | Style |
| --- | --- | --- | --- | --- | --- | --- | --- |
| Michigan Pros.[2] | 180 | 2 | 2.8 | 360 | Yes | Ankle | Pros. |
| BLEEX[3,4] | 175* | n.r. | 2.50 | 200 | No | Ankle | Exo. |
| Vanderbilt Pros.[5] | 130 | n.r. | 2.50† | 250 | No | Ankle | Pros. |
| MIT Pros.[6,7] | 120 | 3.8 | 2.50 | 350 | No | Ankle | Pros. |
| Michigan Exo.[8] | 120 | 2 | 1.37 | n.r. | Yes | Ankle | Exo. |
| MIT AFO[9] | 120 | n.r. | 1.12 | 370 | Backpack | Ankle | Exo. |
| SPARKY[10,11] | 100 | n.r. | 2.70 | 400 | No | Ankle | Pros. |
| MINDWALKER[12] | 100 | 6 | 2.90 | 960 | Yes | n/a | Exo. |
| Anklebot[13,14] | 50 | n.r. | 3.60 | 340 | Yes | Ankle | Exo. |
| RoboKnee[15,16] | 40 | 7.5 | 3.00 | 630 | No | Knee | Exo. |

Table 1: Comparison of candidate joint torque control systems capable of ankle-like torques (at least 40 N·m, or ⅓ the typically-observed values for normal human walking). Peak torque, closed-loop torque bandwidth (−3 dB gain), total mass worn by the human, and peak joint mechanical power are compared to experimental data from the emulator of the present invention. The inventive system is stronger, lighter, more responsive, and more powerful than reported values for all prior systems. Best performance is indicated in bold. The abbreviations n/a and n.r. indicate not applicable and not reported, respectively.

Figure 4:
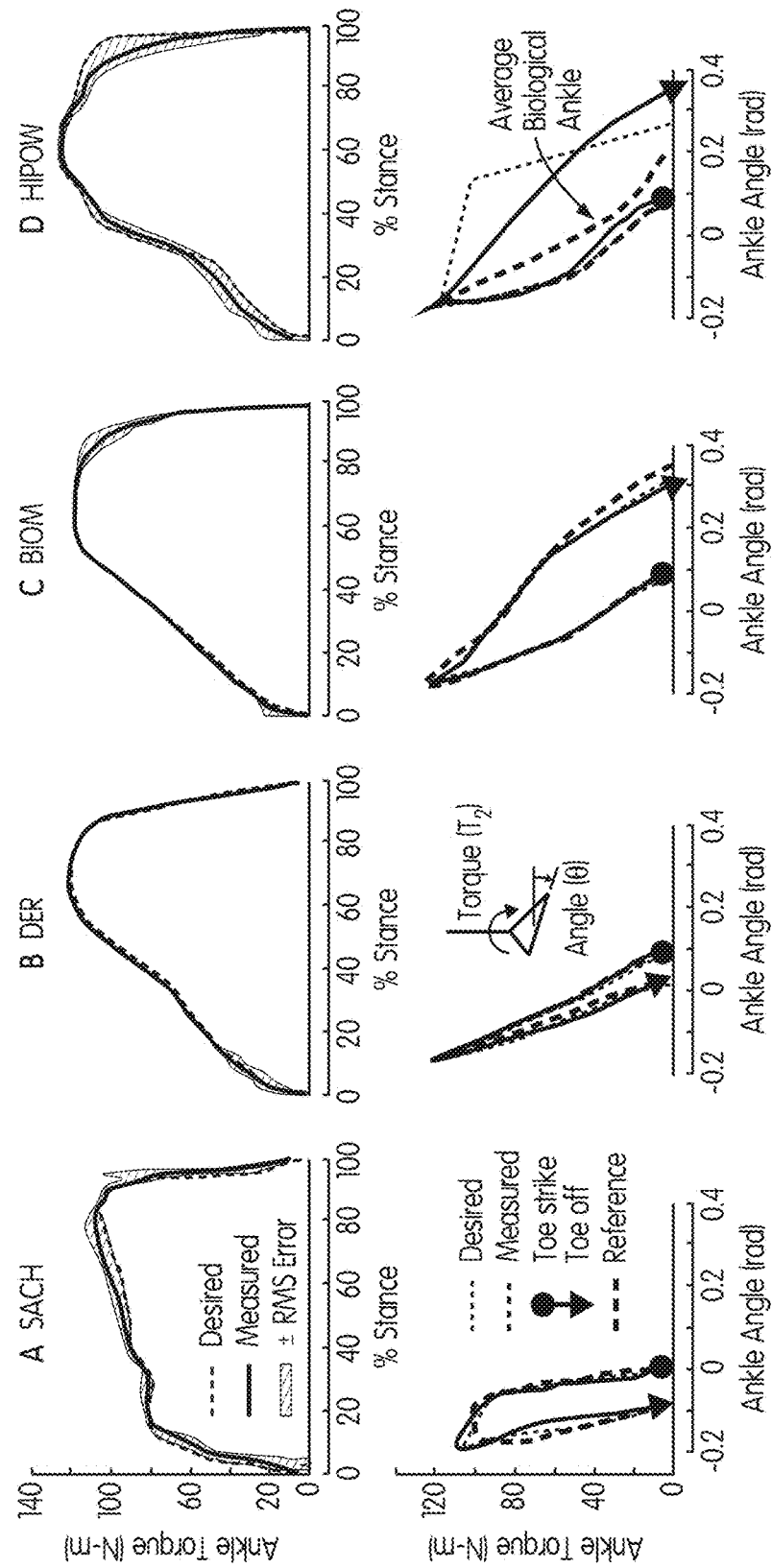
FIG. 4 shows results of testing of an exemplar embodiment of the present invention with test subjects, in particular.

The invention includes methods and systems to distinguish the gait capacity of patients to be fitted with prosthetics. An exemplar system as described above was tested over a range of work outputs on five unilateral amputee subjects. In this experiment, net ankle push-off work was varied from −1.9 to 8.0 times the net work generated by the healthy biological ankle during normal walking, as shown in FIG. 4. For two subjects, metabolic rate was minimized near the level of work provided by the healthy biological ankle; for two subjects, metabolic rate was unaffected by push-off work; and for one subject, increased push-off work increased metabolic rate. These very different effects show the need for device selection based on each individual's response.

In addition to being able to test for different levels of work, the invention incorporates specific emulations of commercial prostheses. To perform such emulations, the invention uses impedance-matching control, in which the ankle's angular stiffness (N·m per radian) is controlled to match a reference value determined from a commercial prosthesis of each class. In the demonstration of the exemplar system, published ankle kinetics data was used to build a reference curve of ankle moment vs. ankle angle for examples of a SACH foot, a DER foot, and the BiOM T2 System foot.

Those skilled in the art will recognize that the present invention could be adapted to include such data from other existing and future prosthetic devices. Also, the system can be extended through expression of finer and finer device categories, ultimately including specific parameters of a given make and model of prosthesis. In such a case, it may be beneficial to have a second assessment in which the prescription is refined to specific values of, e.g., keel or bumper stiffness and damping. Another extension is to add automatic ankle angle adjustment, to identify any advantages to the individual of prostheses that adapt to terrain (e.g. Proprio, élan, Magellan). When additional fully robotic prostheses come to market, realistic emulations of each could be included in the system, so as to identify which specific device suits an individual. The invention could be extended to include multi-degree-of-freedom emulators that provide additional control, for example over center of pressure in the frontal plane The target for the impedance-matching controller was designed using a piecewise-linear approximation to the nonlinear reference curve shown in FIG. 5. The ground contact period was divided into four sub-phases: early and late dorsiflexion and early and late plantarflexion. Each sub-phase was given a separate slope (effective stiffness) and intercept. Transitions from one sub-phase to the next were triggered by the direction of ankle velocity (dorsiflexing or plantarflexing) and by threshold values of ankle angle (early or late). Using different stiffness targets in each sub-phase allowed the reference curve to approximate the stiffness and energy return (or generation) characteristics for each commercial prosthesis. In addition to these emulation modes, we designed a high power condition (HiPow) with significantly greater work output than the natural ankle provides. This mode was designed with a dorsiflexion profile typical of non-amputee walking, but very low stiffness during early plantarflexion (shallow slope), such that the ankle provided high moment over significant deflection, resulting in positive ankle work roughly twice that of the natural ankle. This result is shown in FIG. 4D.

The impedance-matching emulation approach described above yielded good behavior in reproducing target work output, in addition to reproducing moment vs. angle reference behavior from the commercial prostheses, as shown in FIG. 4. Emulations of SACH, DER and BiOM feet were each very close to the reference data (moment vs. time RMS error of 7 N·m, 2 N·m and 4 N·m, respectively). The HiPow mode successfully produced a very high work output and gave users an ambulation experience they could not have had with any other system, though its trajectory tracking performance was slightly worse (RMS error of 8 N·m from its design target). To improve this error, in one embodiment of the invention, iterative learning control is used to reduce the residual errors in target tracking.

In one aspect of the present invention, the system collects data on metabolic rate and/or heart rate of the subject 10 using respirometer and pulse oximeter 20, shown being worn by subject 10 in FIG. 2, while subject 10 is using the emulator on a flat or tilted treadmill 14, to estimate maximum sustainable speed.

In one aspect of the present invention, the system collects data on maximum walking speed, for use in estimating gait capacity.

In one aspect of the present invention, the system includes inertial sensor on the emulator and the contralateral foot to enable assessment of gait stability using variability in stride length, stride width and stride time. Variable cadence is important to high K-level mobility ratings, where greater cadence variability is considered better mobility. At the same time, high kinematic variability within a steady-state task is sometimes associated with fall risk and poor mobility. The assessment protocol of the present invention provides tests of walking ability at different speeds (and hence cadences), and the stride variability data measures gait quality during each condition. This data helps to identify more and less beneficial prosthetic devices for each individual.

In one aspect of the present invention, data is collected on approximate ground reaction force ("GRF") peaks on the prosthetic side foot. GRF outcomes can thereby be reported, such as early and late force peaks, without the need for an instrumented treadmill. GRF peaks are important indicators of gait function such as weight acceptance mechanics and late stance weight support. Comparing force profiles across conditions provides additional evidence for appropriate prosthetic prescription.

In a clinical setting, the use of the present invention begins with an assessment of various emulated prosthetics in a prosthetics clinic or in a hospital. The report, including metrics for effort, maximum sustainable speed, gait stability, ground force peaks, and user and assessor feedback on each condition, will be sent to the physician and the prosthetist. The physician will consider the emulator results alongside traditional indications such as general health, desired activities, specific residual limb properties, balance confidence, and cost. The addition of objective performance results will allow the physician to make better-informed, more appropriate, and more defensible prescriptions. Then, the prosthetist will use the test results to choose specific componentry and tune the prosthesis to meet the patient's documented needs. For example, a subject who achieves high speeds with moderate effort in the DER condition, but demonstrates lateral instability, may be given a DER foot with an especially wide base of support. Or, a subject who can walk twice as fast with the BiOM emulation could be prescribed one based on the large benefit it provides. As another example, a subject whose speeds and efforts are similar with the DER and BiOM emulations could be prescribed a high-quality DER foot, because they may gain more from its durability than from the BiOM's positive work output.

Figure 6:
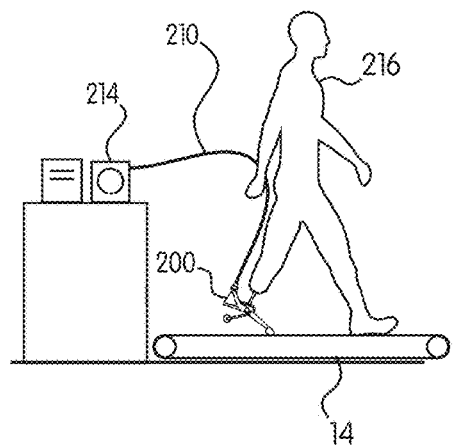
FIG. 6 illustrates a second embodiment of the invention utilizing a mechanical design of the two degree of freedom ankle-foot prosthesis emulator.
Figure 6:
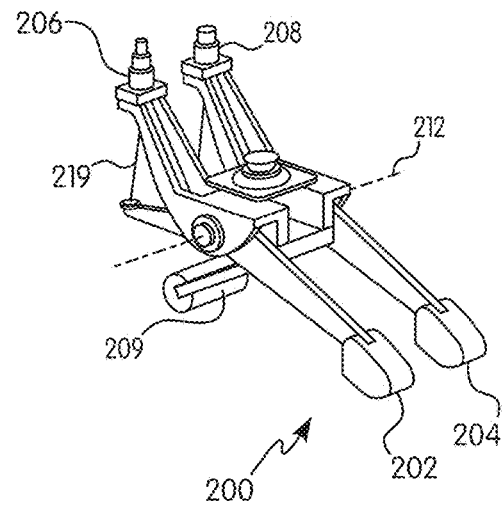
Figure 6:
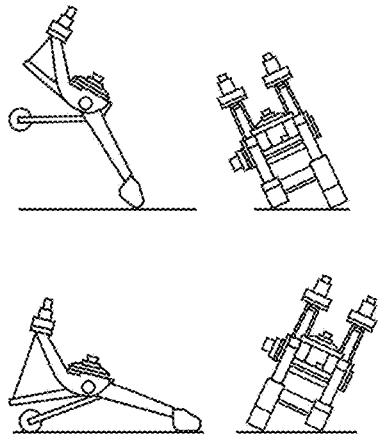
Figure 6:
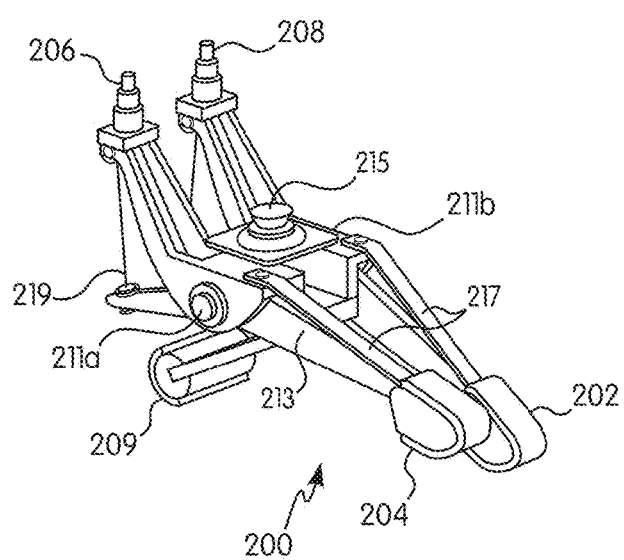

A second embodiment of the invention is shown in FIG. 6, having a lateral forefoot 202 and a medial forefoot 204 which are independently controlled and sensed. The design and evaluation of the robotic ankle-foot prosthesis emulator system has active control of both plantarflexion and inversion-eversion torques and allows inversion-eversion using two articulated forefoot digits. End-effector 200 was integrated with existing off-board motor and control hardware to facilitate high bandwidth torque control. End-effector 200 did not include explicit series elasticity, testing the sufficiency of axial compliance in the tether. A basic walking controller was implemented, intended to evaluate the system's potential for emulating prosthesis behavior during interactions with a human user. This approach was expected to result in validation of a system that can explore new dimensions of prosthesis assistance, particularly those related to balance during walking.

The emulator system consists of off-board actuation and control hardware 214, a flexible Bowden-cable tether 210 and end-effector 200 worn by subject 10. The prosthesis end-effector 200 has two independently-actuated forefoot digits 202, 204 and a separate, passive heel spring 209. Plantarflexion occurs when both digits 202, 204 rotate together, and inversion/eversion occurs when the medial forefoot 204 and lateral forefoot 202 move in opposite directions. Plantarflexion and inversion-eversion torques are proportional to the sum and difference, respectively, of individual forefoot torques. The prototype used in experiments is instrumented with encoders 211a and 211b at each ankle joint and four strain gages 213 in a Wheatstone bridge on each forefoot to measure torque. End-effector 200 is connected to the user via a universal pyramidal adapter 215. Rubber bands 217 dorsiflex the forefoot digits during the swing phase of walking.

End-effector 200 was designed and constructed with torque control in both plantarflexion and inversion-eversion directions. As with the first embodiment, the actuation and control hardware is located off-board so as to keep worn mass low. Flexible Bowden-cable tethers 210 transmit mechanical power to the prosthesis but do not interfere with natural movements of the limb.

End-effector 200 achieves torque and motion in both plantarflexion and inversion-eversion directions using two independent forefoot digits 202 and 204. The digits share a single axis of rotation 212 similar to the plantarflexion axis in the human ankle joint, and are spaced mediolaterally such that one is closer to the centerline of the body, as shown in FIG. 6B. Plantarflexion occurs when both digits rotate in the same direction, and inversion-eversion occurs when the digits rotate in opposite directions, as shown in FIG. 6C. For purposes of this embodiment of the invention, plantarflexion angle is defined as the average of the forefoot angles and the inversion-eversion angle as the difference between the forefoot angles multiplied by the ratio of forefoot length to half the foot width. Similarly, plantarflexion torque, $\tau_{pl}$, is defined as the sum of the lateral and medial forefoot torques, $\tau_l$ and $\tau_m$, while inversion torque, $\tau_{inv}$, is defined as the difference between the lateral and medial forefoot torques multiplied by the ratio of half the foot width, ½ w, to forefoot length, l, or $$\tau_{pl} = \tau_l + \tau_m \tag{1}$$

$$\tau_{inv} = \frac{w}{2l}(\tau_l - \tau_m)$$

The end-effector 200 consists of a frame, two forefoot digits with revolute joints, and a compliant heel 209. The frame of the device is connected to the pylon or socket of subject 10 via universal pyramidal adapter 215. The frame houses needle roller bearings for ankle joints, which have a double-shear construction. Each forefoot is long and thin, tapers towards its ends, and has an I-beam cross section, making it well-suited to three-point bending. One end of the forefoot contacts the ground, while the other end is acted on by cable 219 (only one shown in FIG. 6), with the hinge located in the middle. When cable 219 pulls upward on the posterior aspect of the forefoot, a moment is generated. The conduit of cable 219 presses down on the frame equally and oppositely, such that the foot experiences no net force from the transmission. Rubber bands 217 act to dorsiflex the forefoot when the transmission allows, such as during the swing phase. A separate, unactuated heel spring 209 is connected to the frame. Rubber-coated plastic pads are attached to the ends of the heel and forefoot digits for better ground contact. The frame and forefoot digits were machined from 7075-T6 aluminum, the heel spring was machined from fiberglass (GC-67-UB, Gordon Composites), and the forefoot pads were fabricated using fused-deposition modeling of ABS plastic. The cable is preferably a Bowden-style cable.

The dimensions of end-effector 200 were based on an average male human foot. In the test embodiment, the device measures 0.23 m in length, heel to forefoot tip, 0.07 m in width, forefoot center to forefoot center, and 0.08 m in height, from ground to ankle joint. The forefoot length, from axis of rotation to tip, is 0.14 m. Ankle range of motion is −20 to 30 in plantarflexion and greater than −20 to 20 in inversion-eversion. End-effector 200 weighs approximately 0.72 kg.

Medial and lateral forefoot joint angles were sensed individually using digital absolute magnetic encoders (MAE3, US Digital). Forefoot torques were sensed using strain gages 213 (SGD-3, Omega Engineering), configured in a Wheatstone bridge, with two gages on the top and bottom surfaces of each forefoot midway between the tip and the ankle joint. Strain gauges 213 measure strain in each rotating forefoot component. A calibration is then performed to map strain gauge measurements to ankle torque (they are related linearly by the stiffness of the forefoot component).

Bridge voltage was amplified (FSH01449, Futek Advanced Sensor Technology, Inc.), sampled at a frequency of 5000 Hz and low-pass filtered with a cutoff frequency of 100 Hz. Plantarflexion and inversion/eversion angles and torques were calculated in software from medial and lateral forefoot values.

Forefoot digits 202, 204 are actuated through independent Bowden cable tethers 210 and off-board motors, allowing independent control of medial forefoot 204 and lateral forefoot 202 torques. Plantarflexion and inversion-eversion torques can be independently controlled, but maximum allowable inversion-eversion torque is proportional to plantarflexion torque. When inversion-eversion torque is zero, the plantarflexion torque is divided evenly between the forefoot digits. As inversion torque increases towards its limit, the torque on lateral forefoot 202 approaches the total desired plantarflexion torque, while the torque on medial forefoot 204 approaches zero. When inversion (or eversion) torque equals plantarflexion torque divided by 2l/w, the inversion-eversion torque cannot be increased further, as doing so would require negative torque on the medial (or lateral) forefoot, and negative ground reaction forces. This defines a feasible region of inversion torques as a function of plantarflexion torque (FIG. 7).

Figure 7:
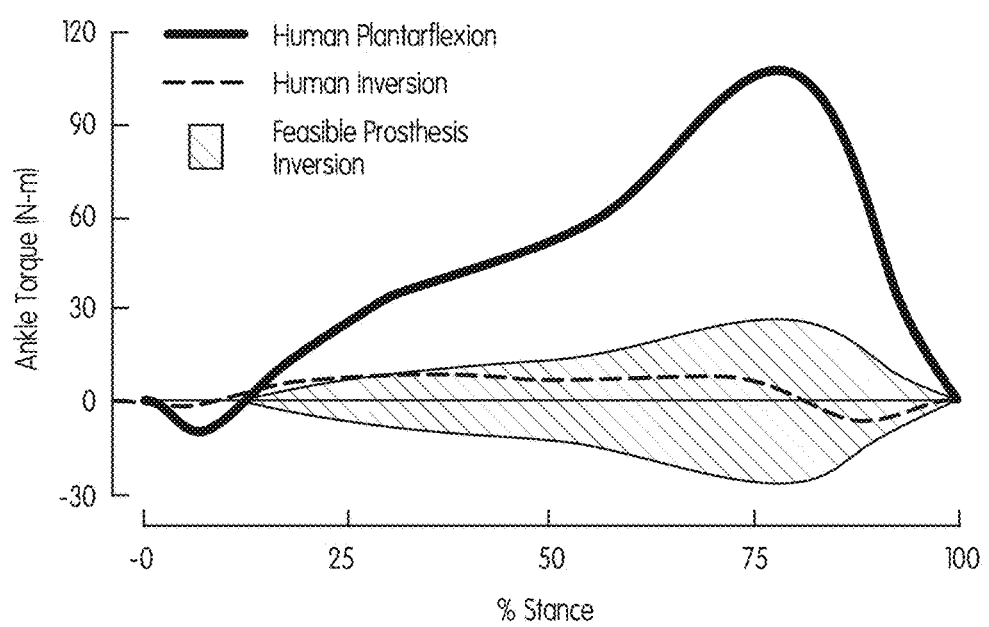
FIG. 7 shows coupling between prosthesis plantarflexion and inversion-eversion torque illustrated with typical human walking data.

FIG. 7 shows coupling between prosthesis plantarflexion and inversion-eversion torque illustrated with typical human walking data. Maximum feasible inversion/eversion torque (gray region) is proportional to plantarflexion torque (Eq. 1). With a typical plantarflexion torque pattern (solid line) the typical inversion-eversion torque (dashed line) falls within the feasible region for this device. Reference data for human walking at 1.6 m/s were used.

Classical feedback control was used to regulate torque during benchtop tests, with an additional iterative learning term during walking trials. Desired torque for each forefoot was first calculated from desired plantarflexion and inversion-eversion torques. Motor velocities were then commanded using proportional control on forefoot torque error. Motor velocity is similar to the rate of change in forefoot torque, owing to compliance between the off-board motor and prosthesis forefoot. During walking trials, an additional time-based iterative learning term was added, which provided feed-forward compensation of torque errors that tended to occur at the same time each step.

In walking trials, torque control was used during stance and position control was used during swing. Initial forefoot contact was sensed from an increase in forefoot torque upon making contact with the ground. During the ensuing stance period, desired inversion-eversion torque was set to a constant value, providing a simple demonstration of platform capabilities.

Desired plantarflexion torque during stance was calculated as a function of plantarflexion angle so as to approximate the torque-angle relationship observed during normal walking. The end of the ground contact was detected when plantarflexion torque crossed a minimum threshold. During the ensuing swing phase, the forefoot digits were position controlled to provide ground clearance.

Benchtop tests were conducted to characterize device performance in terms of torque measurement accuracy, response time, bandwidth, and disturbance rejection. Walking trials were performed to assess mechatronic performance under similar conditions as expected during biomechanics experiments.

Torque measurement calibration was performed by applying known forces to the end of each forefoot using free weights and fitting amplified strain gage bridge voltage to applied torque. Measurement accuracy was characterized in a separate validation test as root mean squared (RMS) error between applied and measured forefoot torques.

Step response tests were performed in which the prosthesis frame and forefoot digits were rigidly fixed and commanded desired torque as a square wave from 0 to 180 N·m in plantarflexion or −20 to 20 N·m in inversion/eversion. Trials were conducted for each direction and computed the mean and standard deviation of the 90% rise and fall times.

Bandwidth tests were performed in which desired torque was commanded as a 0 to 40 Hz chirp, oscillating between 10 and 90 N·m for plantarflexion and between −20 and 20 N·m for inversion-eversion. An exponential chirp was used to improve signal to noise ratio in the low frequency range. The desired and measured torque was transformed into the frequency domain using a Fast Fourier Transform and the magnitude ratio and phase difference was used to generate a Bode plot. The gain-limited and phase-limited bandwidths were calculated as the frequencies at which the amplitude ratio was −3 dB and the phase margin was 45°, respectively. Trials were performed for both torques and calculated crossover frequency means and standard deviations.

A test intended to evaluate the torque errors that would arise from unexpected disturbances to forefoot position was also performed. It was expected that high series stiffness in this system might have provided high bandwidth at the cost of higher sensitivity to position disturbances, for example during initial forefoot contact with the ground. The forefoot digits were placed on opposite ends of a seesaw-like testing jig such that forefoot forces were equal and forefoot motions were equal and opposite. A 0 to 25 Hz chirp was applied in medial forefoot position, oscillating between 0° and 5° of plantarflexion (or 0 and 0.012 m of forefoot tip displacement) and commanded a constant desired torque of 30 N·m to the lateral forefoot. The amplitude of the resulting torque error was transformed into the frequency domain using a Fast Fourier Transform, reported as a percent of the constant desired torque magnitude. The frequency at which error rose above 30% of the desired torque was calculated, analogous to the −3 dB (70% amplitude) criteria used in bandwidth tests.

Walking trials were performed to evaluate torque tracking performance under realistic conditions. One subject (67 kg, 1.77 m tall, 23 yrs, male) without amputation wore the device using a simulator boot. Five walking trials were conducted in which desired inversion/eversion torque, $\tau_{inv}$ was commanded as: Maximum, 15 N·m, 0 N·m, −15 N·m, and Maximum Negative. The magnitudes of Maximum and Maximum Negative inversion-eversion torque were proportional to plantarflexion torque at each instant in time. The subject walked on a treadmill at 1.25 m/s for 100 strides in each condition. Each step was normalized to percent stance period and calculated an average step for each condition. Torque tracking error was characterized as both the RMS error across the entire trial and as the RMS error of the average step. Human biomechanical response was not measured, since this study was intended to evaluate performance of the robotic system and not the effects of a proposed intervention.

Figure 8:
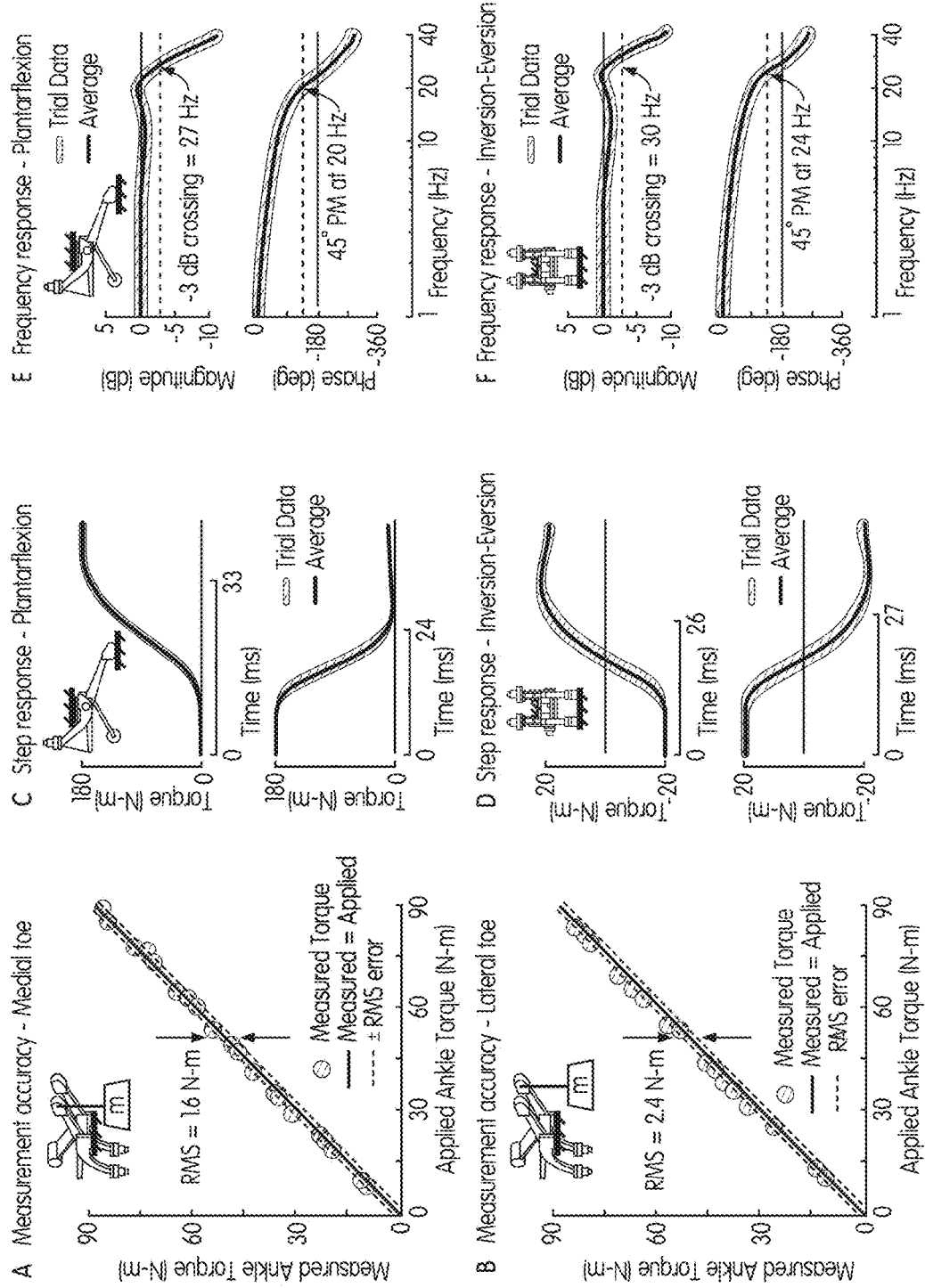
FIG. 8 presents benchtop tests demonstrate low torque measurement error. high peak torque and high closed-loop torque bandwidth in both plantarflexion and inversion-eversion directions.

FIG. 8 shows results of benchtop tests to demonstrate low torque measurement error, high peak torque and high closed-loop torque bandwidth in both plantarflexion and inversion-eversion directions. Peak plantarflexion torque was at least 180 N·m, and inversion-eversion torque had a range of at least 20 to 20 N·m. Rise and fall times ranged from 0.024 to 0.033 s. Bode plots for closed-loop control of E plantarflexion and F inversion-eversion torque, calculated from responses to 90 N·m and ±20 N·m magnitude chirps in desired torque, respectively. Bandwidth ranged from 20 to 30 Hz, limited by 45° phase margin.

The benchtop tests revealed low torque measurement error, high peak torque and high closed-loop torque bandwidth. The root mean squared (RMS) torque measurement errors for medial and lateral forefoot digits were 1.64 N·m and 2.43 N·m, respectively, following calibration (FIGS. 8A & 9B). The 90% rise and fall times between 0 and 180 N·m in plantarflexion torque were 0.033±0.001 s and 0.024±0.001 s (mean±s.d.), with 0.5% and 1.6% overshoot, respectively, as shown in FIG. 9C. The 90% rise and fall times between −20 to 20 N·m in inversion-eversion torque were 0.026±0.002 s and 0.027±0.002 s.d. with 3.0% and 3.2% overshoot, respectively, as shown in FIG. 9D. With desired plantarflexion torque oscillating between 10 and 90 N·m, the −3 dB magnitude and 450 phase margin crossover frequencies were 27.2±0.2 Hz and 20.3±0.3 Hz, respectively (FIG. 8E). With desired inversion-eversion torque oscillating between −20 and 20 N·m, the −3 dB magnitude and 450 phase margin crossover frequencies were 29.8±0.2 Hz and 23.8±0.3 Hz, respectively, as shown in FIG. 8F.

Figure 9:
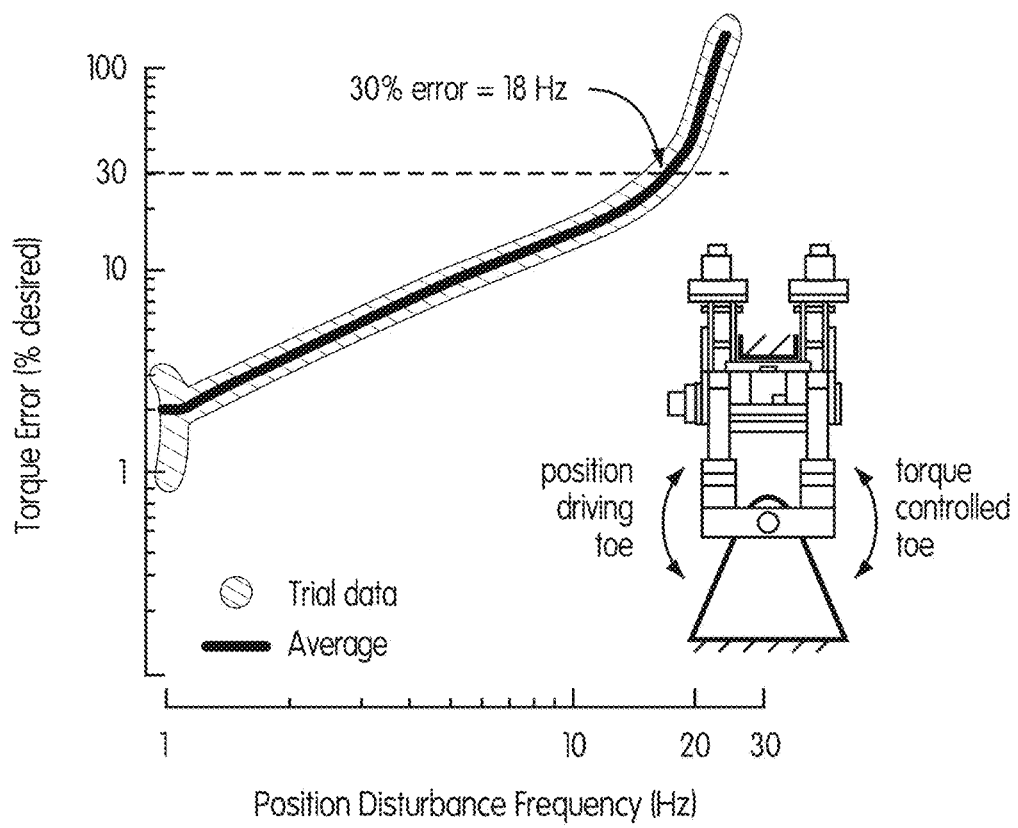
FIG. 9 shows a graph depicting disturbance rejection.

FIG. 9 shows disturbance rejection, depicted as the relationship between torque error (% of the constant desired value) versus the frequency of an applied disturbance in forefoot position. This characterizes the ability of the system to reject unexpected environmental disturbances, such as from sudden contact with the ground. Torque error was less than 30% of the desired value of 30 N·m for disturbance frequencies up to 18 Hz.

Referring to FIG. 9, when a 0.012 m amplitude chirp disturbance was applied in forefoot endpoint position and commanded a constant desired torque of 30 N·m, torque error was less than 30% up to a disturbance frequency of 18 Hz. This disturbance frequency and amplitude are similar to unexpected contact with stiff ground at a rate of 1.4 m/s.

Figure 10:
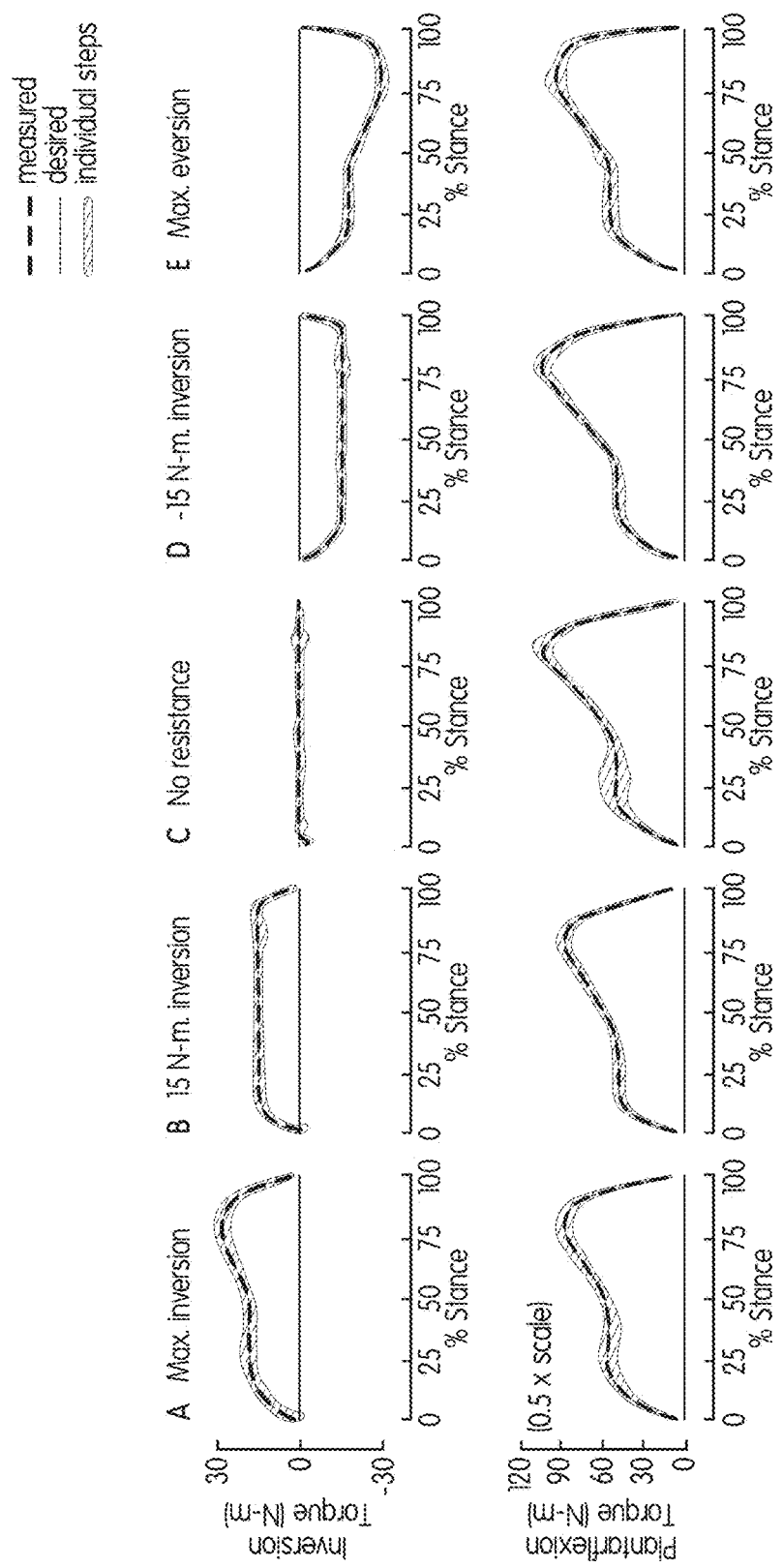
FIG. 10 presents graphs depicting torque tracking during walking experiments.

FIG. 10 presents torque tracking during walking experiments. Desired ankle inversion torque was set to A Maximum, B 15 N·m, C zero, D −15 N·m, and E Maximum Negative, while desired plantarflexion torque was a consistent function of ankle plantarflexion angle. Maximum and Maximum Negative allowable inversion torque were limited by desired plantarflexion torque, since forefoot ground reaction forces could not become negative. In each 100-stride trial, measured torque closely matched desired torque, with RMS errors of at most 3.7 N·m in plantarflexion and 1.1 N·m in inversion-eversion across conditions. Differences between average torque and individual-step torques were dominated by changes in desired torque arising from natural variability in the subject's gait pattern.

Referring now to FIG. 10, during walking trials, subject 10 walked comfortably with the prosthesis while five levels of constant desired inversion-eversion torque were applied. Torque tracking errors in both plantarflexion and inversion-eversion directions were low across all conditions, with maximum RMS errors across the entire trial of 3.2 N·m (3.7% of peak) in plantarflexion torque and 1.1 N·m (3.8% of peak) in inversion-eversion torque, as shown in Table 2.

TABLE 2

| Inversion-Eversion Torque | Plantarflexion Torque Tracking | | | | Inversion-Eversion Torque Tracking | | | |
|---|---|---|---|---|---|---|---|---|
| | RMS Error | % $\tau_{error}$ | AVG RMS Error | % $\tau_{error}$ | RMS Error | % $\tau_{error}$ | AVG RMS Error | % $\tau_{error}$ |
| $\tau_{inv}$ = Maximum | 3.2 ± 1.1 N·m | 3.7% | 1.3 N·m | 1.0% | 1.1 ± 0.4 N·m | 3.8% | 0.4 N·m | 1.6% |
| $\tau_{inv}$ = −15 N·m | 1.0 ± 0.4 N·m | 2.2% | 0.7 N·m | 0.8% | 0.9 ± 0.2 N·m | 5.9% | 0.7 N·m | 4.4% |
| $\tau_{inv}$ = 0 | 2.9 ± 1.7 N·m | 2.8% | 0.6 N·m | 0.6% | 0.8 ± 0.2 N·m | — | 0.5 N·m | — |
| $\tau_{inv}$ = 15 N·m | 2.9 ± 0.8 N·m | 2.8% | 0.9 N·m | 0.9% | 0.8 ± 0.2 N·m | 5.6% | 0.3 N·m | 2.1% |
| $\tau_{inv}$ = Neg. Max. | 3.0 ± 0.9 N·m | 3.3% | 1.3 N·m | 1.4% | 1.0 ± 0.3 N·m | 3.3% | 0.4 N·m | 1.6% |

In a second embodiment of the invention, the end-effector includes two torque-controlled forefoot digits and a torque-controlled heel, wherein the actuation of the three digits allows the adjustment of the origin and magnitude of the resultant force vector. When the emulator has full ground contact, the origin of the vector can be approximately controlled within a support triangle, shown in FIG. 15, which has a maximum length (anterior-posterior) of 0.20 m and a maximum width (medio-lateral) of 0.074 m. The peak force magnitude is approximately 2300 N. The emulator utilizes vertical translation, sagittal rotation, and frontal rotation to maintain full ground contact for about 70% of stance time. This embodiment could be used in experiments investigating of load acceptance mechanics, manipulation of roll-over shape, and control of center of pressure trajectory.

Figure 11:
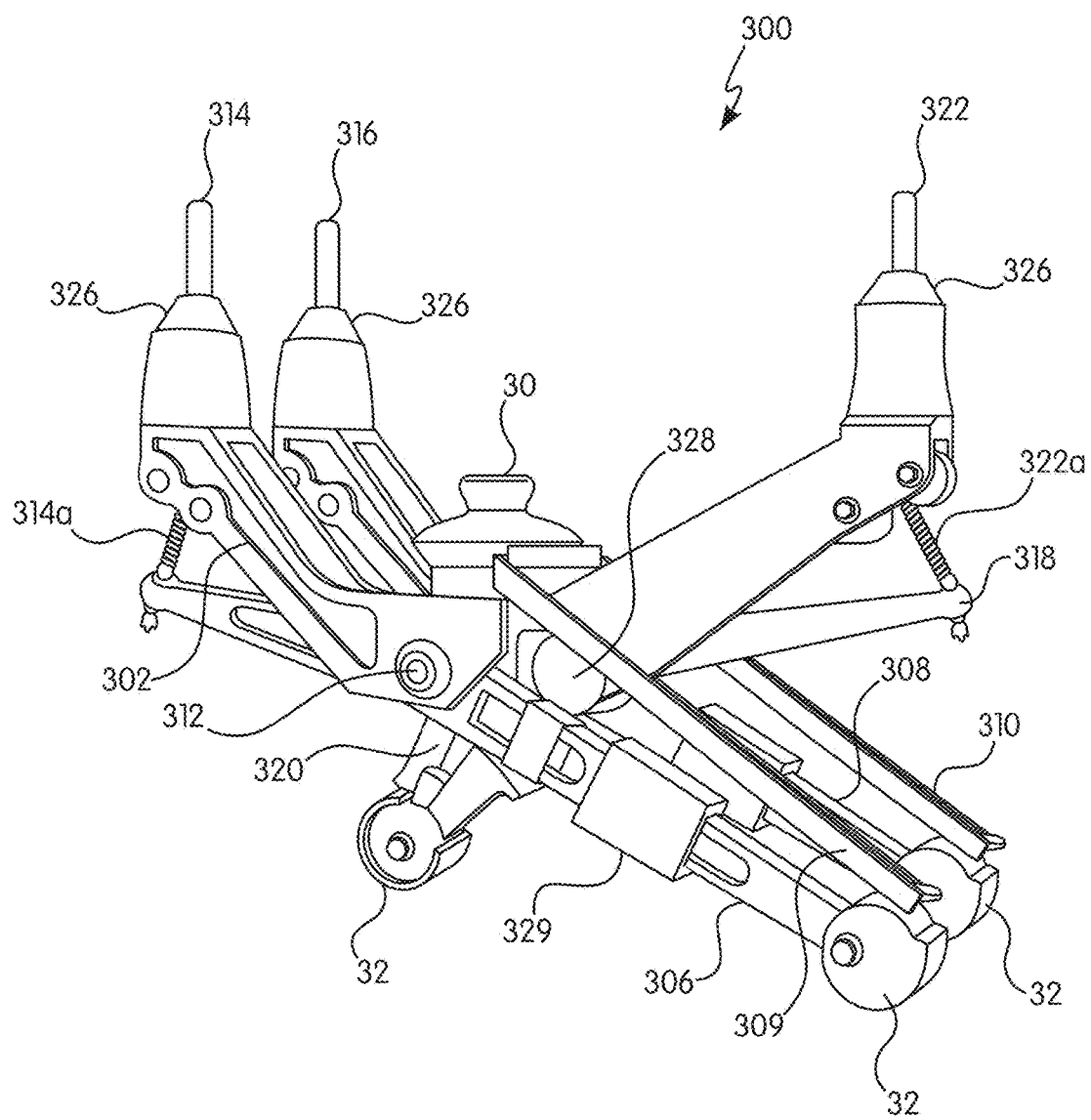
FIG. 11 shows the detail of the construction and components of the end-effector for the three-digit embodiment of the emulator.

In the second embodiment, end-effector 300, shown in FIG. 11, is centered around frame 302, Lateral forefoot 306 and a medial forefoot 308, as well as heel 318 are joined to frame 302 via revolute joint 312. All three digits are independently controlled and sensed.

Each forefoot/heel (digit) acts as a lever wherein one end is pulled up by the motor-controlled cable, which results in a ground reaction force at the other end. Lateral forefoot 306 is controlled by cable 412, having rope 314a inside. Medial forefoot 308 is likewise controlled by cable 316 (rope not shown) and heel 318 is controlled by cable 322, having rope 322a inside. The other side of cables 314, 316 and 322 are attached to motors 338, 340 and 342 respectively, shown in FIG. 12. Preferably, cables 314, 316 and 322 are Bowden cables consisting of a steel outer conduit and a Vectran inner rope.

Retraction springs 309, 310 and 320 connected respectively to lateral forefoot 306, medial forefoot 308 and heel 318, oppose the actuation to take up slack in the inner ropes.

Frame 302 consists of two mirrored frame halves joined by a connecting bridge. Joint torques are measured via strain gauge bridges 329 and joint angles are measured via rotary encoders 328. Strain gauges 329, as shown in FIG. 11, are covered by a protective housing.

Heel 318 is preferably equipped with a limited-slip heel pad 32, which allows the rubber on the bottom of the heel to slide smoothly instead of scrubbing against the ground and wearing out. Additionally, each cable 314, 316 and 322 is equipped with a strain relief 326, which prevents the outer conduit from bending at sharp angles and fatiguing over time.

An off-the-shelf pyramid adapter 30, mounted ion the bridge of frame 302, attaches end-effector 300 to the pylon on the user's existing prosthetic socket.

Figure 12:
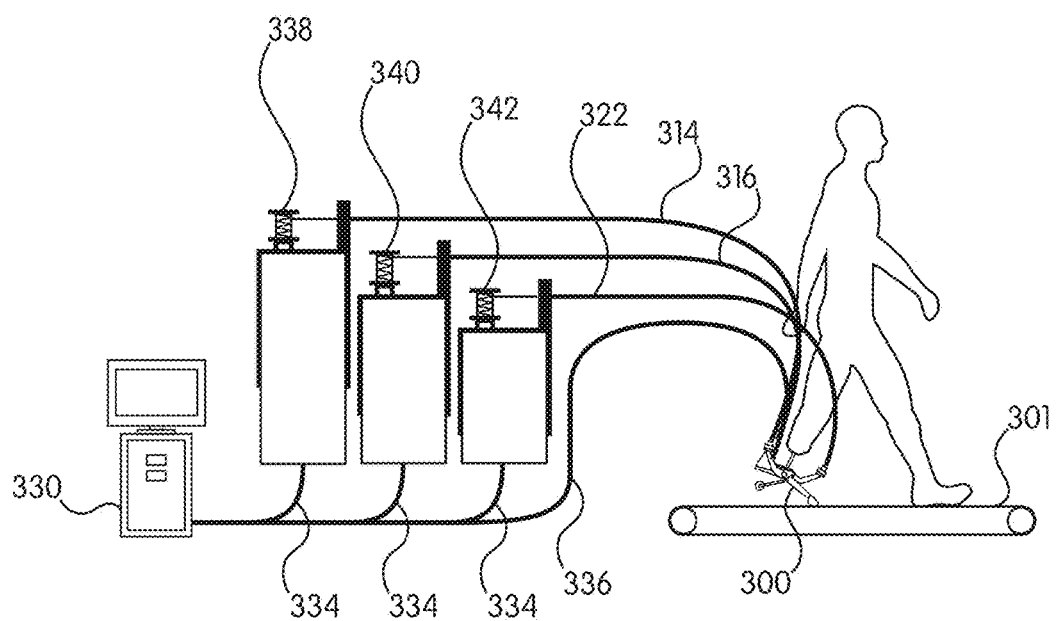
FIG. 12 shows an overall system diagram of the three degree of freedom embodiment of the emulator, including the controller, motors and end-effector.

End-effector 300 is controlled by an off-board system, shown in FIG. 12, very similar to that of the first embodiment, shown in FIG. 2. Off board motors 338, 340 and 342 control digits 3076, 308 and 318 respectively on end-effector 300 under closed-loop computer control implemented as software running in computer 330. Tether 336 provides input signals from encoder 328, and strain gauges 329, as well as any other sensors mounted on end-effector 300. Cables 334 convey signals to control the torque generated by motors 338, 340 and 342.

Using off-board motors 338, 340 and 342 and controller 330 allows a more flexible, much higher-performance system with a simpler design and less body-mounted mass than an untethered system. In a preferred embodiment, controller 330 contains models of a plurality of commercially-available prosthesis and is able to simulate the feel of these prostheses to the subject.

In operation, the subject attached end-effector 300 to the user's existing prosthetic socket and the subject then walks on moving treadmill 301. Feedback is collected via cable 336.

The dimensions of the end-effector were chosen to match the size of a typical human foot and the angles were chosen to exceed the range of motion found in normal walking. The heel-to-forefoot length of the end-effector was chosen to match the heel-to-metatarsal length of atypical foot, similar to the design of commercial prosthetic feet. End-effector 300 was designed to be lightweight while still being able to generate the forces equivalent to a 200 lb subject walking at 1.25 m/s with a factor of safety of >1.5.

Figure 13:
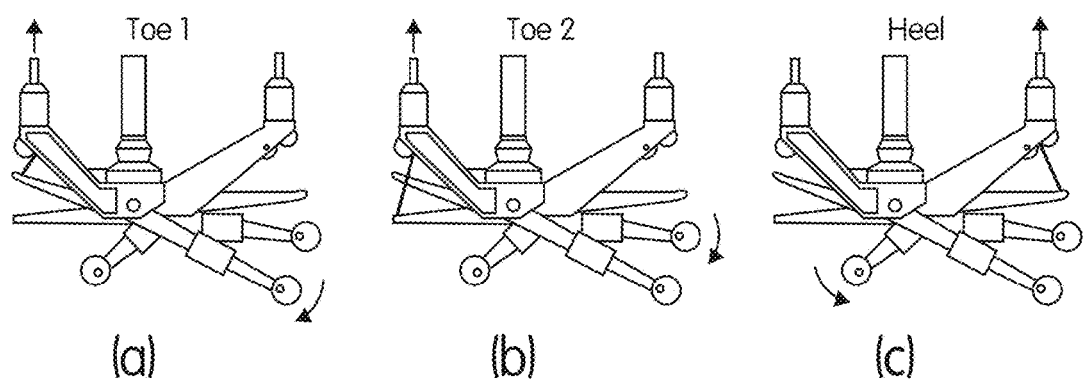
FIG. 13 shows the three degrees of freedom of movement of the ankle-foot embodiment of the emulator, including two forefoot digits and a heel digit.
Figure 14:
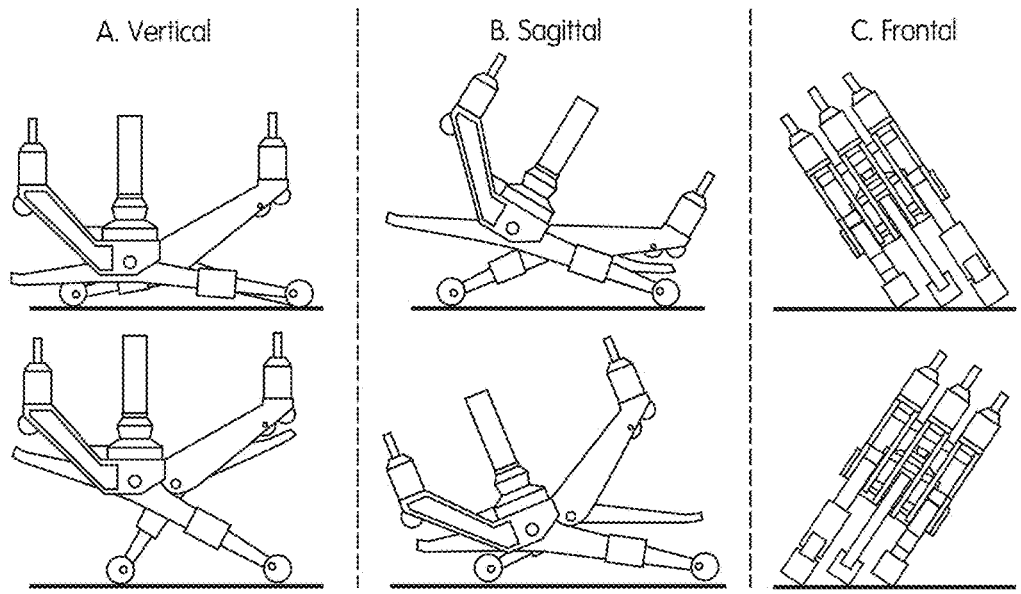
FIG. 14 shows the three modes of movement of the three degree of freedom embodiment of the emulator.
Figure 15:
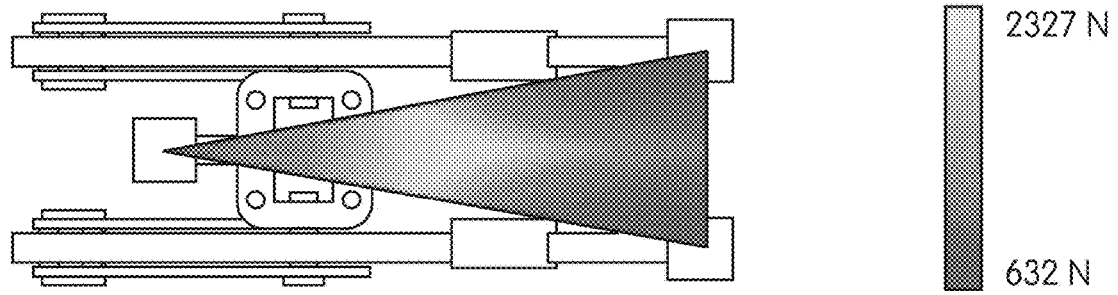
FIG. 15 shows the support triangle formed by the contact points of the heel and two forefoot digits in the three degree of freedom embodiment of the emulator.

End-effector 300 has three active degrees of freedom, as shown in FIG. 13(a-c), which can be expressed in terms of modes of movement or resultant force control. The modes of movement include vertical translation, shown in FIG. 14(a), sagittal rotation, shown in FIG. 14(b) and frontal rotation, shown in FIG. 14(c). Force control includes approximate origin and magnitude control of the resultant force vector. The origin is located in the ground plane and is bounded by the support triangle of the emulator, as shown in FIG. 15.

Full control over the orthogonal component of the force produced by each digit can be controlled, but the total resultant force vector is affected by both orthogonal and parallel components of all three digits. This uncertainty will lead to deviations in the expected origin, magnitude, and direction of the resultant force vector. However, the desired and actual resultant force vectors will be similar if the parallel force components are small.

The weight of end-effector 300 is approximately 1.14 kg, not including the tethers. In terms of modes of movement, the vertical range of translation is approximately 0.050 m, the sagittal range of rotation is approximately −32° to 26° counterclockwise from horizontal, and the frontal range of rotation is approximately ±57° from vertical. In terms of force control capabilities, the maximum length and width of the support triangle is preferably 0.20 m and 0.074 m and the peak force magnitude is approximately 2300 N. Peak force magnitude decreases as the support triangle becomes smaller or if the force origin approaches the edge of the triangle. Resultant force magnitudes can also be expressed in terms of planar torques. Peak dorsiflexion, plantarflexion, and inversion-eversion torques are 68 Nm, 195 Nm, and ±24 Nm.

These results only include configurations where the emulator has all three digits in contact with the ground. The emulator is expected to achieve full ground contact for about 70% of stance time.

The emulator described here as the second embodiment approximately controls the location and magnitude of the resultant force over a long portion of stance phase. This control allows the emulator to investigate concepts such as load acceptance mechanics. For example, this emulator could be used to vary the energy dissipated during the beginning of stance phase.

This emulator is able to produce high forces while still maintaining a worn mass roughly equivalent to that of an average human foot and half of that of commercially-available mobile powered prostheses with one controlled degree of freedom.

Although the invention is illustrated and described herein with reference to specific embodiments, the invention is not intended to be limited to the details shown of specific embodiments described. In particular, it will be realized by one of skill in the art that various modifications may be made in the details and implementation without departing from the invention.

We claim:

1. A system for assessing the gait capacity of user lower leg amputees, comprising:
   an end effector, attachable to a user, the end effector having a plurality of digit portions rotatably attached to a platform about a pivot point;
   a first motor corresponding to a first digit portion of the plurality of digit portions;
   a second motor corresponding to a second digit portion of the plurality of digit portions;
   a first cable coupling the first motor to the first digit portion, the first cable configured to apply a first actuating force to the first digit portion;
   a second cable coupling the second motor to the second digit portion, the second cable configured to apply a second actuating force to the second digit portion;
   wherein the first motor is configured to provide the first actuating force independently from the second motor being configured to provide the second actuating force;
   a controller, for controlling the first motor independently from the second motor; and one or more sensors, mounted on the end effector, the one or more sensors configured to send data regarding one or more operation parameters of the end effector to the controller.

2. The system of claim 1 further comprising one or more subject sensors, attached to the user, the subject sensors configured to send data regarding one or more physical parameters of the subject to the controller.

3. The system of claim 1 wherein the one or more sensors are configured to collect data regarding rotational angles of one or more digit portions of the plurality of digit portions.

4. The system of claim 2 wherein a subject sensor of the one or more subject sensors is configured to collect data regarding one or more of a respiration and a blood oxygen level of the user.

5. The system of claim 1 wherein the controller is configured to store data comprising one or more models of one or more prostheses and wherein the controller is configured to simulate the operation of the one or more prostheses by controlling the first motor, the second motor, or both the first and second motors.

6. The system of claim 1 further comprising a treadmill configured to measure speed data representing a walking speed of the user, the treadmill further configured to send the speed data to the controller.

7. The system of claim 1 wherein the one or more sensors are configured to measure a strain force on the first digit portion, the second digit portion, or both the first and second digit portions.

8. A device for assessing the gait capacity of user lower leg amputees, comprising:
  a platform supporting a mounting for rigidly fixing the device to the leg of a user;
  a plurality of digit portions comprising a first digit portion and a second digit portion;
  one or more sensors configured for sensing an angle of rotation of the first digit portion the second digit portion, or both the first and second digit portions about a pivot point;
  a first motor corresponding to the first digit portion of the plurality of digit portions by a first linkage and configured to apply a first tensioning force to the first digit portion by the first linkage;
  a second motor corresponding to the second digit portion of the plurality of digit portions by a second linkage and configured to apply a second tensioning force to the second digit portion by the second linkage;
  a first spring member attached between the first digit portion and the platform, wherein the first spring member is tensioned when the first motor applies the first tensioning force to the first digit portion; and
  a second spring member attached between the second digit portion and the platform, wherein the second spring member is tensioned when the second motor applies the second tensioning force to the second digit portion.

9. The device of claim 8 further comprising:
  a controller configured to control the first motor, the second motor, or both the first and second motors, the controller configured to control first motor, the second motor, or both the first and second motors to vary the amount of work done by a user walking with the device;
  wherein the controller is configured to receive data from the one or more sensors representing a rotation of one or both of the first and second digit portions.

10. The device of claim 9 wherein the controller is configured to receive data representing one or more physical characteristics of the user.

11. The device of claim 10 wherein the one or more physical characteristics includes a respiration measurement and a blood oxygen level of the user.

12. The device of claim 9 wherein the controller is configured to store data comprising one or more models of prostheses and is further configured to cause one or both of the first and second motors to simulate one or more characteristics of the one or more prostheses by varying the first tensioning force, the second tensioning force, or both the first and second tensioning forces.

13. A device for assessing the gait capacity of user lower leg amputees, comprising:
  a platform supporting a mounting for rigidly fixing the device to the leg of the user;
  a lateral toe portion, rotatably attached to the platform at a pivot point, the lateral toe portion having a first end for contacting a walking surface and a second end extending past said pivot point;
  a lateral linkage, attached to the second end of the lateral toe portion;
  a medial toe portion, rotatably attached to the platform at a pivot point, the medial toe portion having a first end for contacting a walking surface and a second end extending past the pivot point;
  a medial linkage, attached to the second end of the medial toe portion;
  a heel portion, rotatably attached to the platform at a pivot point, the heel portion having a first end for contacting a walking surface and a second end extending past the pivot point;
  a heel linkage, attached to the second end of the heel portion;
  a lateral motor, attached to the lateral linkage, for applying tension to the second end of the lateral toe portion;
  a medial motor, attached to the medial linkage, for applying tension to the second end of the medial toe portion; and
  a heel motor, attached to the heel linkage, for applying tension to the second end of the heel portion.

14. The device of claim 13 further comprising:
  a lateral spring, attached at one end near the first end of the lateral toe portion and at an opposite end to the platform;
  a medial spring, attached at one end near the first end of the medial toe portion and at an opposite end to the platform; and
  a heel spring, attached at one end near the first end of the heel portion and at an opposite end to the platform.

15. The device of claim 13 further comprising:
  a lateral sensor, for sensing an angle of rotation of the lateral toe portion about the pivot point;
  a medial sensor, for sensing an angle of rotation of the medial toe portion about the pivot point; and
  a heel sensor, for sensing an angle of rotation of the heel portion about the pivot point.

16. The device of claim 15 further comprising:
  a controller for controlling the lateral motor, the medial motor and the heel motor, the controller being configured to individually control each of the motors to vary the amount of work done by the user walking with the device;
  wherein the controller is configured to receive data from one or more of the lateral, medial, and heel sensors representing the respective angles of rotation of the lateral toe portion, the medial toe portion and the heel portion.

17. The device of claim 16 further comprising:
a lateral tension encoder for sensing a tensioning force applied by the lateral motor to the lateral toe portion; and
a medial tension encoder for sensing a tensioning force applied by the medial motor to the medial toe portion;
wherein the lateral tension encoder and the medial tension encoder are each configured to send encoded tension data to the controller.

18. The device of claim 17 wherein the controller is configured to store data comprising one or more models of prostheses and further wherein the controller is configured to cause one or more motors to simulate one or more characteristics of the one or more prostheses by varying tensioning forces applied to the lateral and the medial toe portions and the heel portion.

19. The device of claim 17 further comprising a treadmill configured to measure speed data representing a gait speed of the user, the treadmill configured to send the speed data to the controller.

20. A system for assessing the gait capacity of user lower leg amputees, comprising:
an end effector, attachable to a user, the end effector having a plurality of digit portions rotatably attached to a platform about a pivot point;
one or more motors corresponding to one or more respective digit portions of the plurality of digit portions, the one or more motors being located off-board relative to the end effector;
one or more cables respectively coupling the one or more motors to the one or more respective digit portions, the one or more cables configured to apply one or more respective actuating forces to the one or more respective digit portions;
a controller, for controlling the one or more motors; and
one or more sensors, mounted on the end effector, the one or more sensors configured to send data regarding one or more operation parameters of the end effector to the controller.

21. The system of claim 20 further comprising one or more subject sensors, attached to the user, the subject sensors configured to send data regarding one or more physical parameters of the subject to the controller.

22. The system of claim 21 wherein a subject sensor of the one or more subject sensors is configured to collect data regarding one or more of a respiration and a blood oxygen level of the user.

23. The system of claim 20 wherein the one or more sensors are configured to collect data regarding rotational angles of one or more digit portions of the plurality of digit portions.

24. The system of claim 20 wherein the controller is configured to store data comprising one or more models of one or more prostheses and wherein the controller is configured to simulate the operation of the one or more prostheses by controlling one or more motors.

25. The system of claim 20 further comprising a treadmill configured to measure speed data representing a walking speed of the user, the treadmill further configured to send the speed data to the controller.

26. The system of claim 20 wherein the one or more sensors are configured to measure a strain force on the one or more respective digit portions of the plurality of digit portions.

* * * * *

UNITED STATES PATENT AND TRADEMARK OFFICE
CERTIFICATE OF CORRECTION

PATENT NO. : 10,350,092 B1
APPLICATION NO. : 15/333463
DATED : July 16, 2019
INVENTOR(S) : Vincent Chiu et al.

Page 1 of 1

It is certified that error appears in the above-identified patent and that said Letters Patent is hereby corrected as shown below:

In the Claims

Column 17, Line 38, Claim 8, after "portion" insert -- , --

Column 18, Line 5, Claim 11, delete "includes" and insert -- include --

Signed and Sealed this
Eighth Day of October, 2019

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 10,350,092 B1 |
| APPLICATION NO. | : 15/333463 |
| DATED | : July 16, 2019 |
| INVENTOR(S) | : Caputo et al. |

It is certified that error appears in the above-identified patent and that said Letters Patent is hereby corrected as shown below:

In the Specification

Column 1, under STATEMENT REGARDING GOVERNMENT-SPONSORED RESEARCH AND DEVELOPMENT, Lines 17-20, delete "This invention was made with partial government support under NIH grant 1R43HD076518-0, NSF grant CMMI-1300804 and NSF grant CBET1511177. The government has certain rights in this invention." and insert -- This invention was made with United States government support under HD076518 awarded by the National Institutes of Health and CMMI1300804 and CBET1511177 awarded by the National Science Foundation. The U.S. government has certain rights in the invention. --.

Signed and Sealed this
Thirty-first Day of May, 2022

Katherine Kelly Vidal
*Director of the United States Patent and Trademark Office*